US011287332B2

United States Patent
McCall

(10) Patent No.: US 11,287,332 B2
(45) Date of Patent: Mar. 29, 2022

(54) METHOD OF DETERMINING HEAT OF HYDRATION OF A CONCRETE TEST SPECIMEN

(71) Applicant: W. Calvin McCall, Charlotte, NC (US)

(72) Inventor: W. Calvin McCall, Charlotte, NC (US)

(*) Notice: Subject to any disclaimer, the term of this patent is extended or adjusted under 35 U.S.C. 154(b) by 190 days.

(21) Appl. No.: 16/774,678

(22) Filed: Jan. 28, 2020

(65) Prior Publication Data

US 2020/0166417 A1    May 28, 2020

Related U.S. Application Data

(63) Continuation-in-part of application No. 16/502,575, filed on Jul. 3, 2019, now abandoned.

(60) Provisional application No. 62/692,989, filed on Jul. 2, 2018.

(51) Int. Cl.
   *G01K 17/04*   (2006.01)
   *G01N 33/38*   (2006.01)
   *G01N 25/20*   (2006.01)

(52) U.S. Cl.
   CPC ............ *G01K 17/04* (2013.01); *G01N 25/20* (2013.01); *G01N 33/383* (2013.01)

(58) Field of Classification Search
   CPC ....... G01K 17/04; G01N 25/20; G01N 33/383
   See application file for complete search history.

(56) References Cited

U.S. PATENT DOCUMENTS

| | | | | |
|---|---|---|---|---|
| 4,208,907 A * | 6/1980 | Townsend | ............... | G01K 17/00 374/34 |
| 8,532,815 B1 * | 9/2013 | Ciuperca | ................. | B28B 11/24 700/198 |
| 8,794,078 B2 * | 8/2014 | Darbe | ...................... | G01N 3/10 73/803 |
| 9,593,988 B1 * | 3/2017 | Liberman | ............... | G01K 17/00 |
| 9,678,025 B1 * | 6/2017 | Fesmire | ................. | G01N 25/72 |
| 9,766,221 B2 * | 9/2017 | Radjy | ..................... | G01N 25/20 |
| 10,656,109 B1 * | 5/2020 | Fesmire | ................. | G01N 25/18 |
| 11,047,748 B1 * | 6/2021 | Wu | ..................... | G01N 25/4866 |
| 2010/0087827 A1 * | 4/2010 | Baroud | ................... | G01N 27/04 606/93 |
| 2010/0318316 A1 * | 12/2010 | Fesmire | ................. | G01K 17/00 702/136 |

(Continued)

*Primary Examiner* — Nathaniel T Woodward
*Assistant Examiner* — Philip L Cotey
(74) *Attorney, Agent, or Firm* — Shumaker, Loop & Kendrick, LLP

(57) ABSTRACT

An adiabatic concrete calorimeter includes a thermal chamber and a heat well subassembly for being positioned in the thermal chamber. The heat well subassembly includes a test cylinder container and a test cylinder mold adapted to be positioned in the test cylinder container for defining the shape of a concrete test specimen formed in the test cylinder mold. Temperature sensors determine the temperature of the concrete test specimen, and transmit temperature data from the temperature sensors to a controller. Electrically-energized heaters are positioned on a surface of the test cylinder container for applying heat to the test cylinder container. A controller determines heat loss of the concrete test specimen and outputs data to the heaters whereby the heaters supply heat to the concrete test specimen sufficient to compensate for heat losses to an ambient environment and maintain the heat of hydration of the concrete test specimen.

3 Claims, 9 Drawing Sheets

(56) References Cited

U.S. PATENT DOCUMENTS

| | | | |
|---|---|---|---|
| 2011/0007775 A1* | 1/2011 | Wu | G01N 25/4866 374/11 |
| 2013/0192382 A1* | 8/2013 | Bois | G01N 33/383 73/803 |
| 2013/0343734 A1* | 12/2013 | Dock, II | F24H 9/20 392/441 |
| 2015/0266783 A1* | 9/2015 | Ciuperca | B28B 11/245 165/287 |
| 2016/0223512 A1* | 8/2016 | Radjy | G01N 33/383 |
| 2018/0045621 A1* | 2/2018 | Radjy | G08B 21/182 |
| 2018/0238820 A1* | 8/2018 | Ghods | G01N 17/02 |
| 2021/0285904 A1* | 9/2021 | Kobayashi | G01N 25/20 |

* cited by examiner

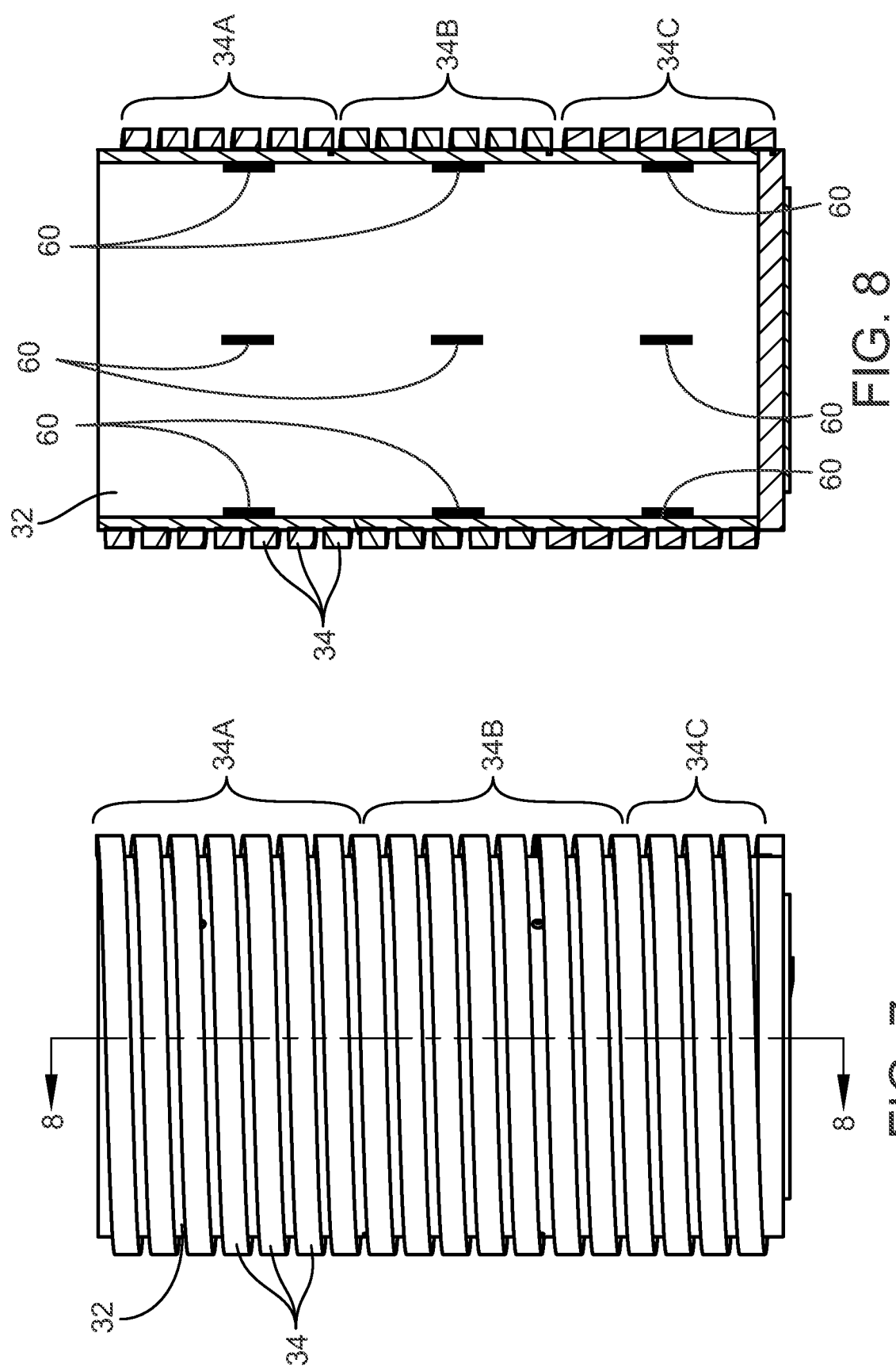

METHOD OF DETERMINING HEAT OF HYDRATION OF A CONCRETE TEST SPECIMEN

CROSS-REFERENCE TO RELATED PATENT APPLICATIONS

This patent application is a continuation-in-part non-provisional application which claims the full benefit of U.S. Provisional Patent Application No. 62/692,989 filed on Jul. 2, 2018, entitled "Adiabatic Concrete Calorimeter and Method", the contents of which are incorporated by reference herein, and U.S. Utility patent application Ser. No. 16/502,575, filed Jul. 3, 2019, the contents of which are incorporated by reference herein.

TECHNICAL FIELD AND BACKGROUND OF INVENTION

This application relates to an apparatus and method of directly measuring the quantity of heat and the rate of heat generation from a concrete specimen. As concrete elements gain strength due to a chemical process, the heat that is generated from this chemical process is typically referred to as the "heat of hydration." For the purposes of this application "heat of hydration" can be defined as the heat that is generated from a specific concrete mixture over a specific period of time. An adiabatic concrete calorimeter is a device that directly measures the quantity of heat and the rate of heat generation from a concrete specimen. The device measures the quantity of heat generated by the concrete specimen by adding or subtracting heat from the calorimeter container. This evaluation method is different from a semi adiabatic calorimeter which measures the heat loss through the calorimeter container and mathematically calculates the temperature of the concrete specimen based on these measured losses.

In certain concrete applications the quantity of the "heat of hydration" needs to be measured. These temperature values are used to determine what, if any, precautions are needed to keep excessive temperatures and differential temperatures from developing between the interior and the surface temperature of the concrete element. These values must be evaluated and monitored so they do not have a detrimental impact on the quality of the concrete element. The heat of hydration values that are measured by the adiabatic concrete calorimeter are used to develop concrete thermal control plans for specific concrete mixtures and specific concrete element sizes.

When testing concrete samples using current technology, the concrete sample gives off its heat of hydration to the surrounding ambient air. This introduces error into the testing process.

There is a need for an apparatus and method of measuring heat of hydration more accurately, efficiently and simply.

SUMMARY OF THE INVENTION

It is therefore an object of the invention to provide an apparatus and method for determining the quantity of heat generated by a concrete specimen by adding or subtracting heat from a calorimeter container.

It is another object of the invention to provide an apparatus and method for determining the quantity of heat generated by a concrete specimen by determining heat of hydration loss to the ambient environment surrounding the test sample and applying heat to the ambient environment sufficient to compensate for heat of hydration that would otherwise be lost to the ambient environment surrounding the test sample.

In accordance with one embodiment of the invention, an adiabatic concrete calorimeter is provided that includes a thermal chamber and a heat well subassembly for being positioned in the thermal chamber and defining an insulation space between interior walls of the thermal chamber and exterior walls of the heat well subassembly. The heat well subassembly includes a test cylinder container and a test cylinder mold adapted to be positioned in the test cylinder container for defining the shape of a concrete test specimen formed in the test cylinder mold. Temperature sensors are positioned on an inner surface of the test cylinder container for sensing the temperature of the concrete test specimen. A plurality of temperature sensors located on the inner surface of the heat well subassembly provide temperature data for the heat well surface adjacent to the test cylinder. Temperature data from the temperature sensors are transferred to a controller which actuates based upon their relative values, and electrically-energized heaters are positioned on a surface of the test cylinder container for applying heat to the test cylinder container. A controller determines the rate and degree of heat loss of the concrete test specimen based on temperature data transmitted from the temperature sensors and outputs data to the heaters whereby the heaters supply heat to the concrete test specimen sufficient to compensate for heat losses to an ambient environment and maintain the heat of hydration of the concrete test specimen.

In accordance with another aspect of the invention, the plurality of temperature sensors are positioned along a vertical extent of the surface of the test cylinder container.

In accordance with another aspect of the invention, the plurality of sensors defines zones in which selected ones of the sensors transmit data to the controller reflecting the temperature of the concrete test specimen in the defined zones.

In accordance with another aspect of the invention, the sensors are spaced in a plurality of vertical tiers at circumferentially-equal angles to each other around an inner side wall of the test cylinder container.

In accordance with another aspect of the invention, the pluralities of heaters are spaced along a vertical extent of the surface of the test cylinder container.

In accordance with another aspect of the invention, the pluralities of heaters comprise a flexible heating element positioned around the outer surface of the test cylinder container.

In accordance with another aspect of the invention, the plurality of heaters define zones in which selected ones of the heaters are adapted to supply heat to the test cylinder container responsive to data from the plurality of sensors reflecting heat lost by the concrete test specimen to ambient environment.

In accordance with another aspect of the invention, the insulation space between interior walls of the thermal chamber and exterior walls of the heat well subassembly includes space above the test cylinder container, between the test cylinder container and the interior walls of the thermal chamber and a bottom of the thermal chamber, and further wherein the insulation space includes an insulation material.

In accordance with another aspect of the invention, the insulation material comprises a microporous insulation material including inorganic silicates and glass fibers.

In accordance with another aspect of the invention, the plurality of temperature sensors consist of detectors selected from the group consisting of resistance temperature detectors, thermistors and thermocouples.

In accordance with another aspect of the invention, the plurality of temperature sensors comprise resistance temperature detectors spaced in vertical and circumferential relation to each other on inner surface of the test cylinder container, and on a cover and bottom of the test cylinder container.

In accordance with another aspect of the invention, an adiabatic concrete calorimeter is provided that includes an enlarged-diameter flange extending laterally outwardly from the top opening of the thermal chamber, the lid includes an enlarged-diameter flange extending laterally outwardly from a centrally positioned void, and at least one connector is provided for connecting the lid to the top opening of the thermal chamber.

In accordance with another aspect of the invention, an adiabatic concrete calorimeter is provided comprising a thermal chamber and a heat well subassembly for being positioned in the thermal chamber and defining an insulation space between interior walls of the thermal chamber and exterior walls of the heat well subassembly. The heat well subassembly includes a test cylinder container for being positioned in the thermal chamber and a test cylinder mold adapted to be positioned in the test cylinder container for defining the shape of a concrete test specimen formed in the test cylinder mold. A plurality of temperature sensors are positioned on an inner surface of the test cylinder container positioned along a vertical extent of the surface of the test cylinder container for sensing the temperature of the concrete test specimen and define zones in which selected ones of the sensors transmit data to the controller reflecting the temperature of the concrete test specimen in the defined zones. The resistance temperature detectors are spaced in vertical and circumferential relation to each other on inner surface of the test cylinder container, and on a cover and bottom of the test cylinder container. A plurality of electrically-energized heaters are positioned on a surface of the test cylinder container and are spaced along a vertical extent of the surface of the test cylinder container for applying heat to the test cylinder container. A controller determines the rate and degree of heat loss of the concrete test specimen based on temperature data transmitted from the temperature sensors and outputs data to the heaters whereby the heaters supply heat to the concrete test specimen sufficient to compensate for heat losses to an ambient environment and maintain the heat of hydration of the concrete test specimen. A data store is provided for recording and storing data transmitted to and from the controller In accordance with another aspect of the invention, the insulation space between interior walls of the thermal chamber and exterior walls of the heat well subassembly includes space above the test cylinder container, between the test cylinder container and the interior walls of the thermal chamber and a bottom of the thermal chamber, and further wherein the insulation space includes an insulation material.

In accordance with another aspect of the invention, a method of determining heat of hydration of a concrete sample is provided and includes the steps of mixing a concrete sample and placing the sample in a mold, placing the mold in an insulated test cylinder, sensing the heat of hydration exotherm and cooling of the concrete sample as it cures, transmitting the heat of hydration exotherm and cooling data of the concrete sample to a data processor, processing the data to determine the amount of heat to apply to the concrete sample to compensate for cooling and to maintain the temperature of the concrete at the heat of hydration exotherm level, recording the heat of hydration data and comparing the heat of hydration of the concrete sample to a standard.

BRIEF DESCRIPTION OF THE DRAWINGS

FIG. 7 is a side elevation of the heat well subassembly shown in FIG. 6;

FIG. 8 is a vertical cross-section of the heat well subassembly shown in FIGS. 6 and 7.

DETAILED DESCRIPTION OF PREFERRED EMBODIMENT

Figure 1:
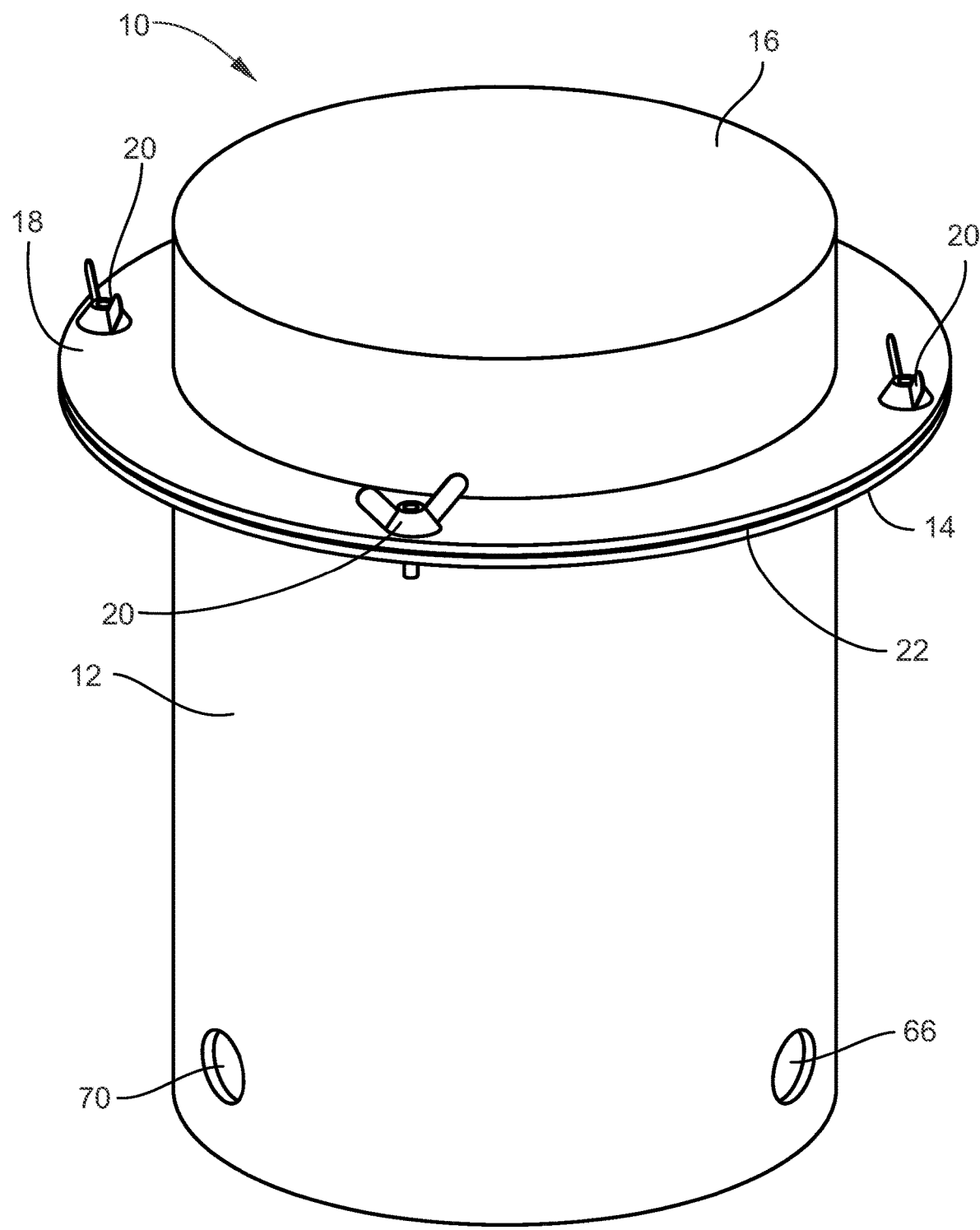
FIG. 1 is a perspective view of an adiabatic concrete calorimeter according to a preferred embodiment of the invention.
Figure 2:
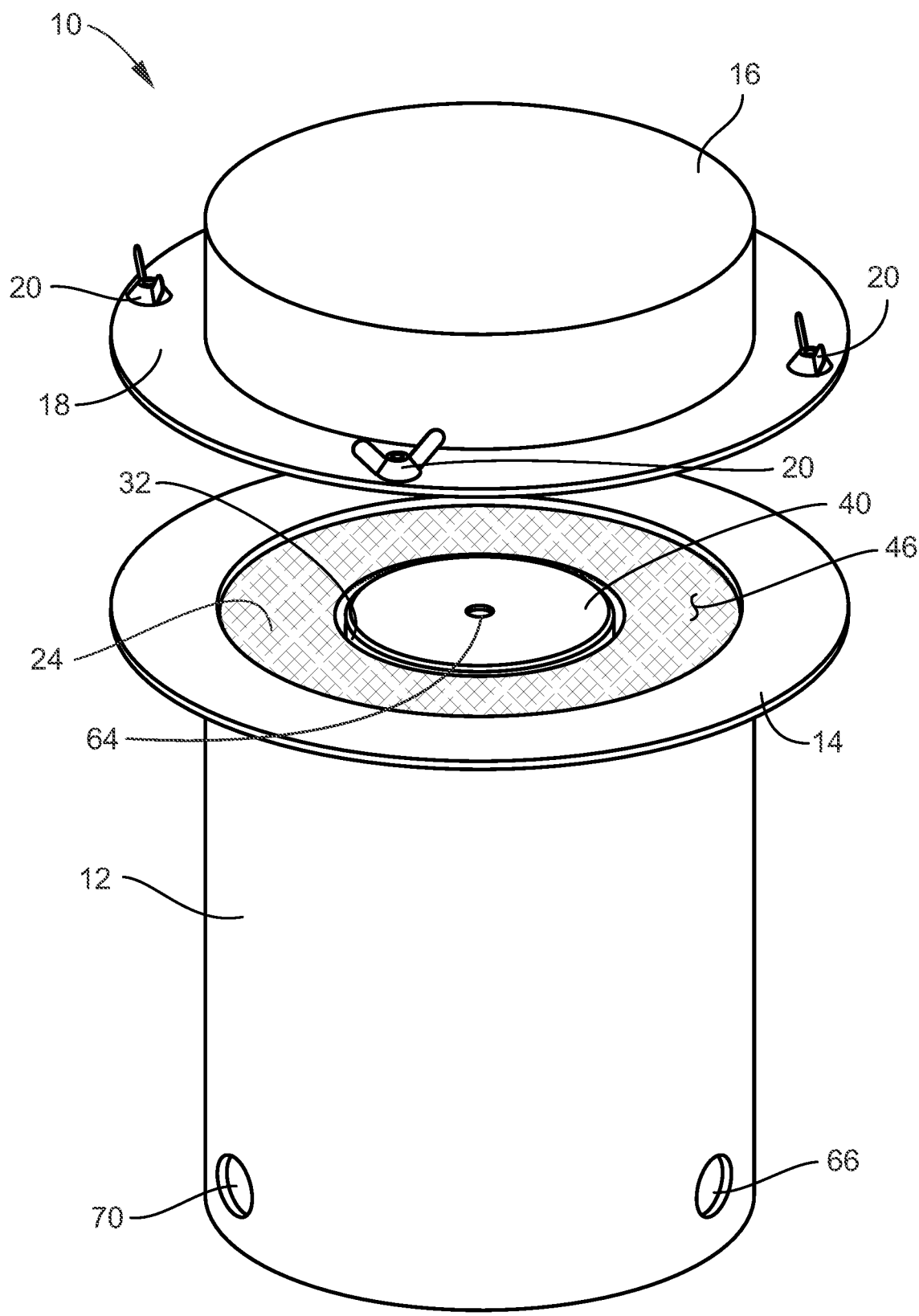
FIG. 2 is a partially-exploded view of the adiabatic concrete calorimeter shown in FIG. 1.
Figure 3:
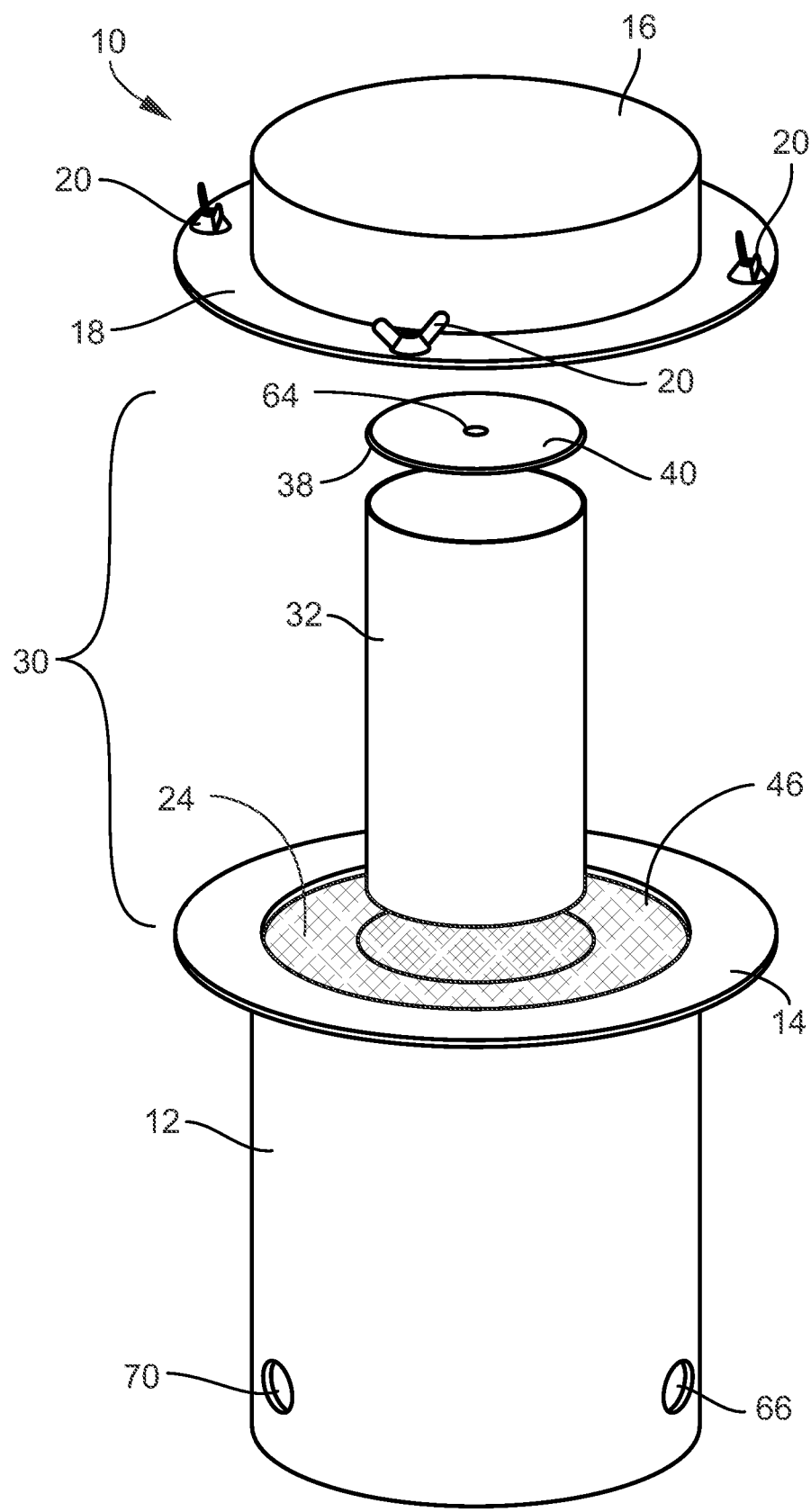
FIG. 3 is a further partially-exploded view of the adiabatic concrete calorimeter shown in FIG. 1.
Figure 4:
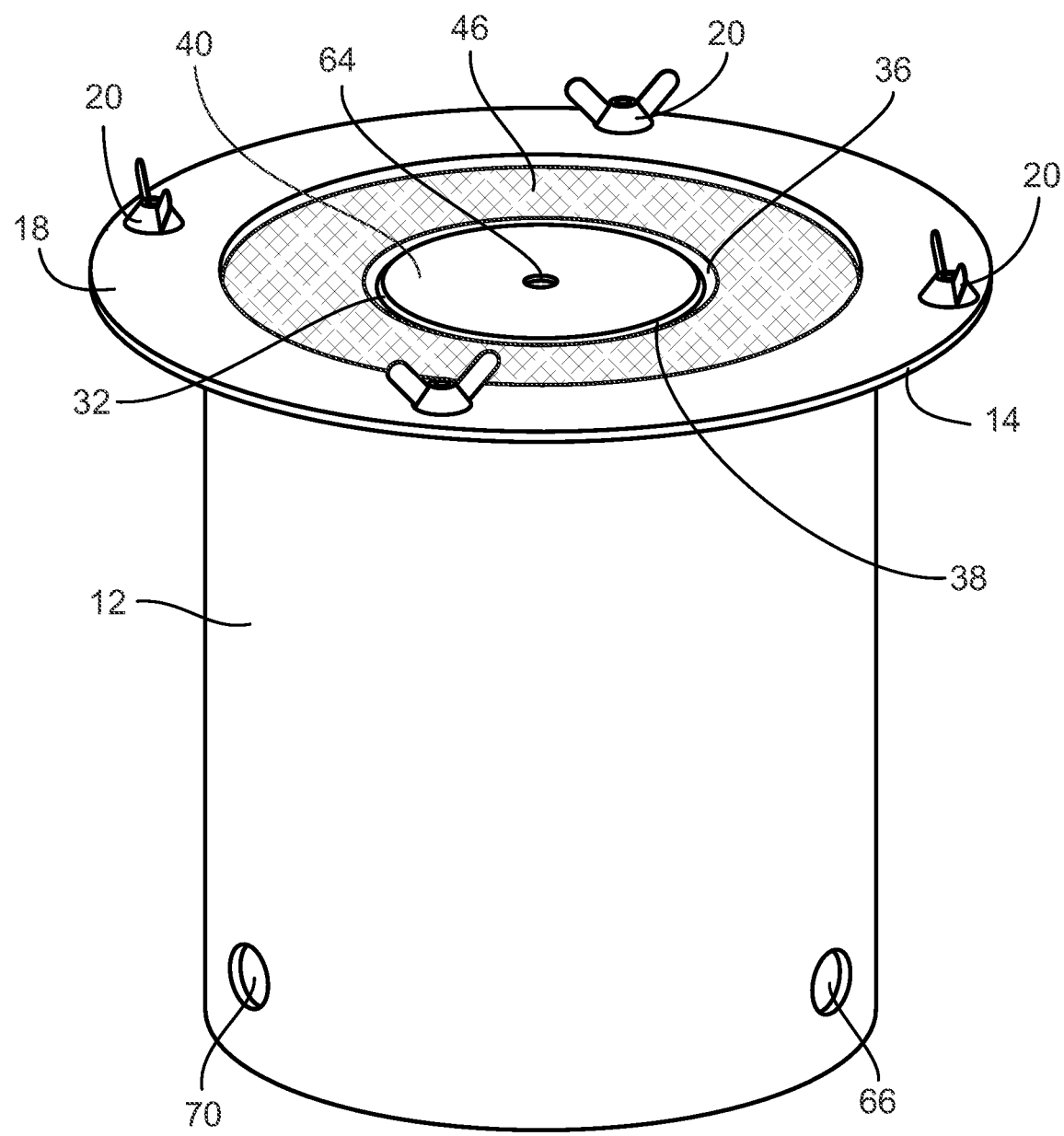
FIG. 4 is a view of the adiabatic concrete calorimeter shown in FIG. 1 with the cover removed.

Referring now to the Figures, an adiabatic concrete calorimeter 10 is shown, and includes a stainless steel thermal chamber 12 having an outwardly-extending flange 14 surrounding its top opening that is adapted to receive and support a removable lid 16. The lid 16 has an outwardly-extending flange 18 secured to the flange 14 of the thermal chamber 12 by a series of spaced-apart bolt and wing-nut assemblies 20. A vapor barrier sheet 22 is positioned between the top surface of the thermal chamber flange 14 and the bottom surface of the lid flange 18 and held in a sealing condition by the tightened wing nut assemblies 20 that force the thermal chamber flange 14 and the lid flange 18 into intimate sealing contact. The thermal chamber 12 includes a void 24 into which a heat well subassembly 30 is placed.

The heat well subassembly 30 includes a test cylinder container 32 wrapped with flexible heating elements 34 in the form of a high temperature silicone over-molded resistive tape that spirals around the container 32 in a vertically spaced-apart configuration. A cylinder mold 36 is contained in the test cylinder container 32 and is used to form a concrete specimen "S" for testing.

The heating elements 34 of the test cylinder container 32 are divided into three vertical zones 34A, 34B and 34C. The test cylinder container 32 is enclosed within the thermal chamber 12 by a cover 38, and a circular flexible silicone heating element 40 is adhesively attached to the cover 38. A circular silicone heating element 42 is adhesively attached to the bottom of the container 32. Together with the three zones 34A, 34B and 34C of the heating element 34, five distinct zones of heat application are provided, as described further below.

The thermal chamber 12 and lid 16 are heavily insulated with insulation batting 46 to reduce thermal loss through the walls of the thermal chamber 12. One suitable insulation material is WDS® Flexipor®, manufactured by Morgan Advanced Materials, a microporous insulation material with an extremely low coefficient of thermal conductivity. WDS® Flexipor® consists of inorganic silicates, such as fumed silica, opacifiers for minimizing infrared radiation and reinforcing glass fibers. WDS® Flexipor® is produced with temperature resistant soluble fiber paper on both sides and wrapped in a polyethylene film for flexibility.

By way of example only, the test cylinder container 32 is constructed of extruded aluminum, has an interior diameter of approximately 7 inches (18 cm), a wall thickness of 0.25 inches (0.6 cm) and a height of 12 inches (30.5 cm). The thermal chamber 10 has an exterior and interior diameter of approximately 13 inches (33 cm) and a height of 18 inches (46 cm), which includes the lid 16, which has a height of 3 inches (7.6 cm). The nominal diameter of the concrete test cylinder 32 is 6 inches (15 cm) in diameter by 12 inches (30.5 cm) in height.

Figure 5:
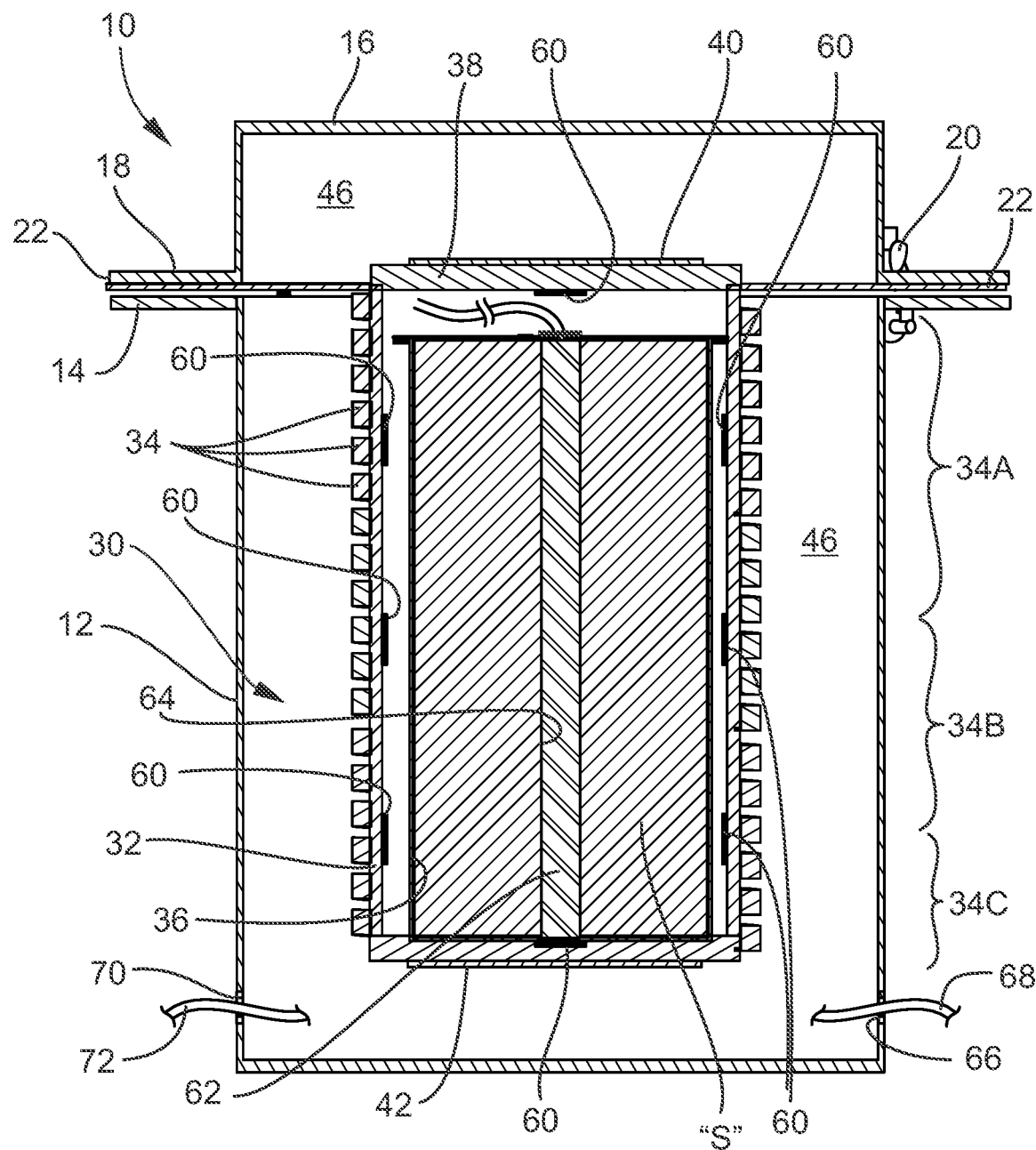
FIG. 5 is a vertical cross section of the adiabatic concrete calorimeter shown in FIG. 1.
Figure 6:
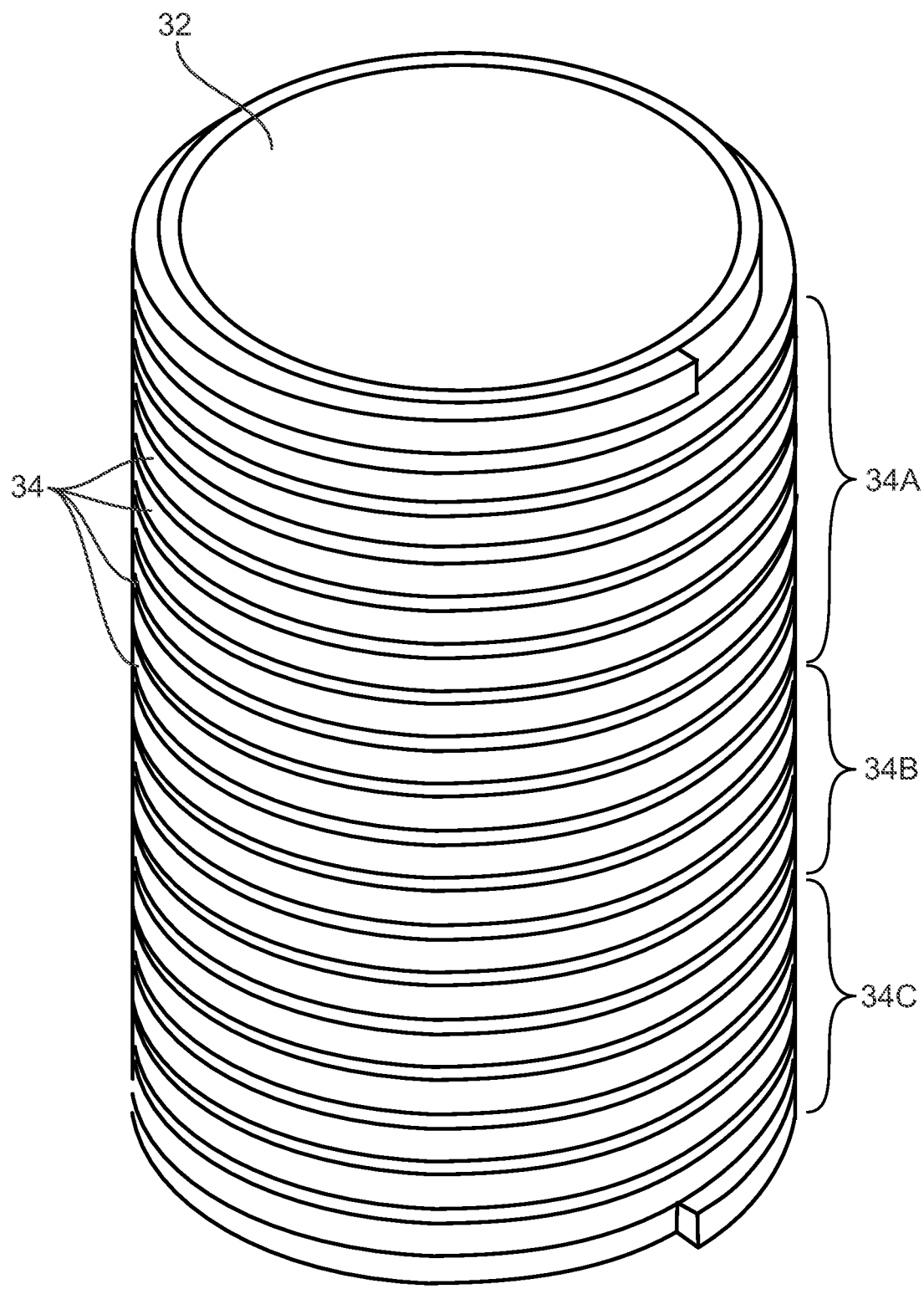
FIG. 6 is a perspective view of the heat well subassembly of the adiabatic concrete calorimeter according to a preferred embodiment of the invention.

As shown in FIG. 5, the test cylinder container 32 includes a means of determining the temperature of the concrete test specimen "S". One method of sensing the temperature is the use of resistance temperature detectors 60 ("RTD"s) positioned in vertically spaced-apart locations on the inner side wall of test cylinder container 32, on the underside of the cover 38 and on the bottom of the cylinder mold 36. According to a preferred embodiment of the invention, the three zones 34A, 34B and 34C are used to define sensor zones, with four RTDs 60 (two shown) spaced in each of three vertical tiers at 90 degree angles to each other around the inner side wall of the test cylinder container 32.

Internal temperature of the concrete specimen "S" is monitored by a probe 62 that extends through the center of the concrete specimen "S" from top to bottom. A bore 64 is formed in the center of the specimen "S" by inserting a rod (not shown) into the center of the cylinder mold 36 and forming the concrete specimen "S" around it. When the specimen "S" has solidified sufficiently the rod is removed and a temperature-sensing probe 62 is inserted into the bore 64 formed by the removal of the rod.

These 12 RTD's 60 together with the RTD's 60 on the on the underside of the cover 38 and on the bottom of the test cylinder 32 and the center probe 62 permit very accurate temperature readings of the specimen "S" as heat of hydration is generated by the curing of the specimen "S".

The thermal chamber 12 includes an access port 66 for a power supply cable 68 supplying current to the heating elements 34, 40 and 42, and an access port 70 for the cabling 72 for the temperature sensors 60 through which the cabling passes and to a control box 80 containing a data storage device, a suitable computing device and read outs. The RTD's or other temperature sensors 60 may be battery-powered or connected to an electrical service. The controller 80 may include wireless capability for transmitting data to a remote location, for example a laptop, smart phone or tablet.

Figure 9:
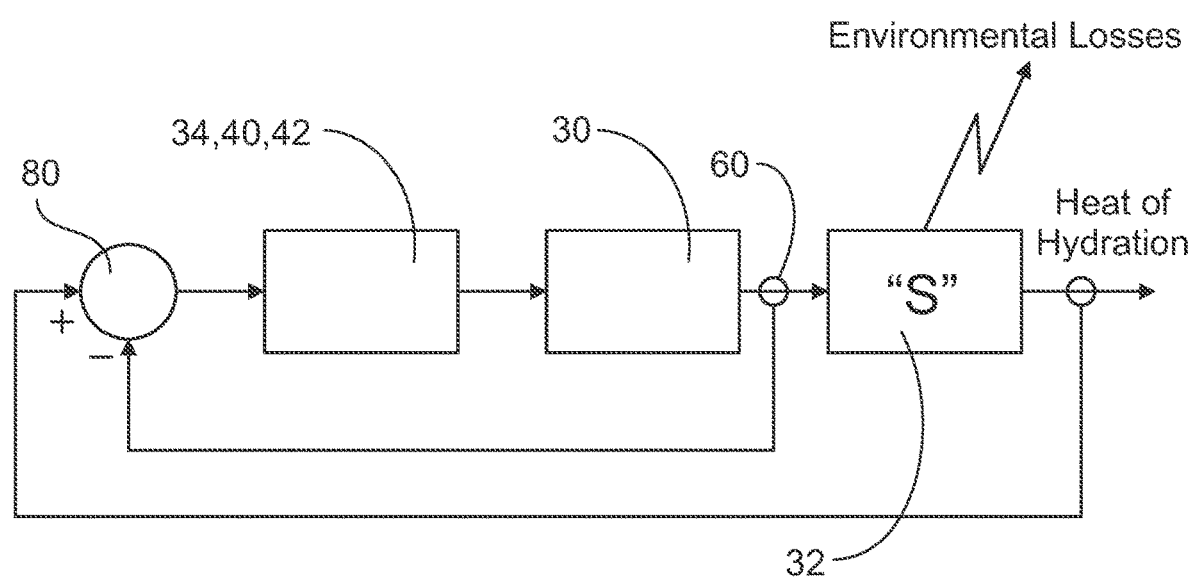
FIG. 9 is a schematic control block diagram of the adiabatic concrete calorimeter according to one embodiment of the invention.

Temperature is sensed by the RTD's 60 and this information is fed to the controller 80 as shown in FIG. 9, and integrated. Sensitivity of the RTD's 60 determines the temperature range within which the concrete specimen "S" will be maintained by the heating elements 34, 40 and 42. Pulse-width modulated (PWM) signals control the current supplied to the heating elements 34, 40 and 42 individually. The temperature signals from the RTD's 60 entering the controller 80 and current output signals from the controller 80 to the heating elements 34, 40 and 42 are recorded and used to document the characteristics of the specimen "S".

The heat of hydration given off by the specimen "S" is the standard, and the apparatus 10 functions to supply that amount of heat to the specimen "S" that exactly matches the amount of cooling of the specimen "S" resulting from heat of hydration losses to the ambient environment.

The controller 80 performs all necessary functions of the calorimeter 10, including calculating necessary heat output based on RTD 60 sensor readings transmitted to the controller 80, records and stores all data, and includes an interface screen by which the controller 80 can be operated.

Figure 10:
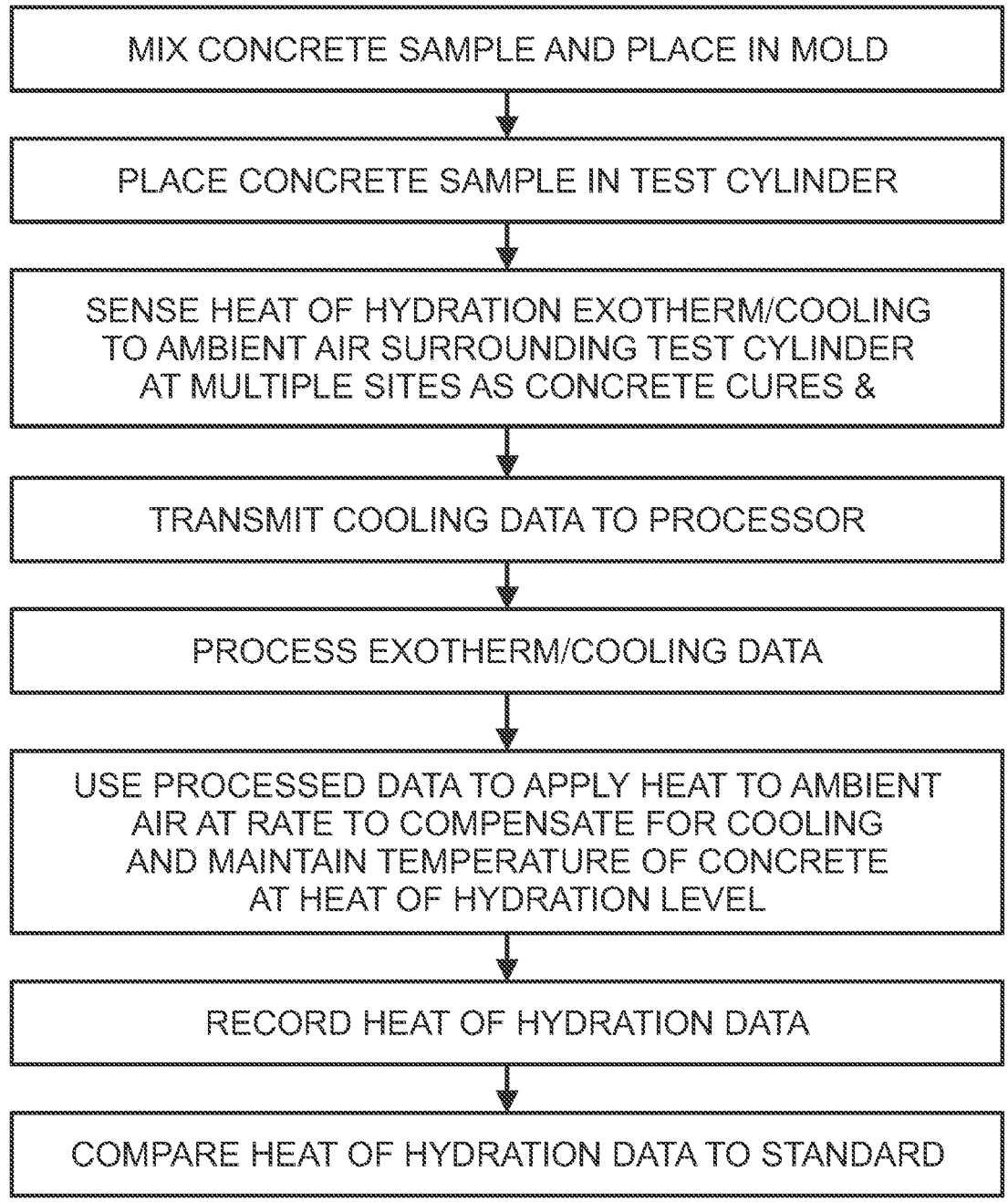
FIG. 10 is a flow diagram illustrating the method steps according to one embodiment of the invention.

As summarized in FIG. 10, a concrete sample is mixed and placed in a cylindrical mold. The concrete sample is placed in a test cylinder. As the concrete cures, the heat of hydration exotherm to ambient air surrounding the test cylinder is sensed at multiple sites around the sample and transmitted to a data processor. The processed data is used to apply heat to ambient air at a rate determined to compensate for cooling and maintain the temperature at the level of the temperature of the hydration as it occurs. This information I recorded and compared to a standard.

An adiabatic concrete calorimeter is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A method of determining heat of hydration of a concrete test specimen, including the steps of:
   (a) providing a set point temperature value for an insulated concrete test specimen test cylinder;
   (b) providing a plurality of internal temperature sensors defining zones in which selected ones of the internal temperature sensors transmit data to a feedback controller reflecting the temperature of the concrete test specimen in the defined zones;
   (c) maintaining the set point temperature value of the insulated test cylinder by operation of the feedback controller to determine the amount of heat to apply to the concrete test specimen to compensate for cooling and to maintain the temperature of the concrete at the heat of hydration exotherm level;
   (d) applying an amount of heat to the concrete test specimen sufficient to compensate for cooling and to maintain the temperature of the concrete at the heat of hydration exotherm level; and
   (e) utilizing the temperature sensors to provide a process value reflecting an environmental temperature condition indicative of a predicted environmental temperature the concrete test specimen may experience under field conditions.

2. A method according to claim 1, and including the steps of:
   (a) providing a set point temperature value for the insulated test cylinder;
   (b) providing a plurality of temperature sensors defining zones in which at least one temperature sensor in each zone provides a temperature set point value for the feedback controller, the feedback controller providing temperature control of the surface temperature of adjacent zones of the insulated test cylinder
   (c) applying an amount of heat to the concrete test specimen sufficient to compensate for cooling and to maintain the temperature of the concrete at the heat of hydration exotherm level; and (d) the temperature sensors indicating the temperature of the concrete test specimen in the plurality of zones.

3. A method according to claim 2 and including the steps of:
(a) determining a maximum internal temperature of the concrete test specimen from a recorded temperature history derived from the internal temperature sensors;
(b) utilizing the maximum internal temperature of the concrete test specimen as the setpoint value for the feedback controller;
(c) utilizing the temperature sensors in the plurality of zones in the insulated test cylinder to provide a process temperature value controlled in a feedback loop to match the maximum concrete sample temperature.

* * * * *